(12) United States Patent
Noheda Marin et al.

(10) Patent No.: US 7,297,788 B2
(45) Date of Patent: Nov. 20, 2007

(54) REGIOSELECTIVE HYDROXYLATION, FUNCTIONALISATION AND PROTECTION OF SPIROLACTAMS

(75) Inventors: Pedro Noheda Marin, Madrid (ES); Manuel Bernabe Pajares, Madrid (ES); Sergio Maroto Quintana, Madrid (ES); Nuria Tabares Cantero, Madrid (ES)

(73) Assignee: Laboratorios Del Dr. Esteve. S.A., Barcelona (ES)

( * ) Notice: Subject to any disclaimer, the term of this patent is extended or adjusted under 35 U.S.C. 154(b) by 218 days.

(21) Appl. No.: 10/853,639

(22) Filed: May 25, 2004

(65) Prior Publication Data

US 2005/0261492 A1    Nov. 24, 2005

(51) Int. Cl.
C07D 205/12 (2006.01)
C07D 221/20 (2006.01)
C07D 209/54 (2006.01)
C07D 491/113 (2006.01)
C07F 7/18 (2006.01)

(52) U.S. Cl. .................. 540/203; 546/16; 548/408
(58) Field of Classification Search .................. None
See application file for complete search history.

(56) References Cited

U.S. PATENT DOCUMENTS

| 4,680,388 A | 7/1987 | Sundeen et al. |
| 5,648,484 A * | 7/1997 | Wu .............................. 540/203 |
| 5,698,548 A * | 12/1997 | Dugar et al. ............ 514/210.02 |

FOREIGN PATENT DOCUMENTS

WO    WO 94/17038    8/1994

OTHER PUBLICATIONS

Miyazaka et al., *Heterocycles*, vol. 59(1), pp. 149-160, Jan. 1, 2003.
Kikugawa et al., *J. Org. Chem.*, vol. 68, pp. 6739-6744, Jul. 26, 2003.
Kwon et al., *J. Org. Chem.*, vol. 67, pp. 3327-3338, 2002.
Green et al., *Protective Groups in Organic Synthesis*, John Wiley & Sons, Inc., New York, NY, pp. v, xi, xii, 1999.
Fischer et al., *J. Org. Chem.*, vol. 52, pp. 4464-4468, 1987.
Wipf et al., *Angew. Chem. Int. Ed. Engl.*, vol. 36(7), pp. 764-767, 1997.
Fischer et al., *Tetrahedron Lett.*, vol. 21, pp. 701-704, 1980.
Carreno et al., *J. Org. Chem.*, vol. 62(26), pp. 9128-9137, 1997.
Mitsunobu, *Synthesis*, pp. 1-28, 1981.
Hughes, *Organic Reactions*, vol. 42, chapter 2, pp. 335-343, 1992.
Snider et al., *J. Org. Chem.*, vol. 63, pp. 6442-6443, 1998.
Braun et al., *Tetrahedron Lett.*, vol. 39, pp. 4667-4670, 1998.
European Patent Office, European search report for EP 04076477.1, Oct. 28, 2004.

* cited by examiner

*Primary Examiner*—Mark L. Berch
(74) *Attorney, Agent, or Firm*—Morgan & Finnegan, L.L.P.

(57) ABSTRACT

The present invention refers to highly functionalised spirofused azetidinones of formula I:

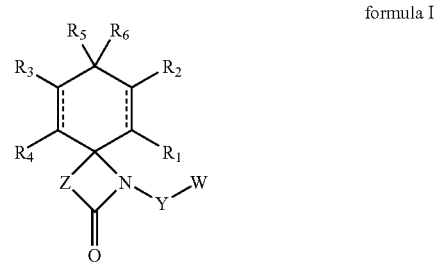

formula I having a cyclohexane moiety with the desired number of protected or unprotected hydroxyl groups which are introduced with high stereo and regioselectivity, as well as processes for their synthesis.

16 Claims, No Drawings

REGIOSELECTIVE HYDROXYLATION, FUNCTIONALISATION AND PROTECTION OF SPIROLACTAMS

FIELD OF THE INVENTION

The present invention relates to new regioselectively hydroxylated, protected and functionalized spirolactams and to processes for their synthesis.

BACKGROUND OF THE INVENTION

Lactams are compounds of high interest due to their biological activities, for example well known β-lactams such as some penicillins, cephalosporins and carbapenems have antibacterial activity.

Spirolactams are one particular class of lactams that have shown interesting biological properties. Some spiro-fused azetidinones have been described as having antibacterial activity, see U.S. Pat. No. 4,680,388, or hypocholesterolemic properties, see for example WO 94 17038. Additionally, if these compounds have adequate functionality, they are valuable intermediates towards different families of compounds. The spirolactam ring is the equivalent of an alpha amino or hydroxy aminoacid and opens many possibilities in diastero and/or enantioselective synthesis.

Miyazawa, E. et al. in *Heterocycles*, vol 59, 1:149-160 "Synthesis of spiro-fused nitrogen heterocyclic compounds via N-methoxy-N-acylnitrenium ions using phenyliodine (III) bis(trifluoroacetate) in trifluoroethanol" describe a process to obtain functionalised spirolactams including some spirodienones.

Kukugawa, Y. e al. in *J. Org. Chem.* 2003, vol. 68, 6739-6744 "Intramolecular cyclization with nitrenium ions generated by treatment of N-acylaminophthalimides with hypervalent iodine compounds: formation of lactams and spirofused lactams" describes the formation of functionalised spirolactams having diene and dienone functionalities.

The conduritols, aminoconduritols, aminoinositols and their derivatives also possess interesting biological properties, some of them have been shown as being antitumoral and antibiotic. Although some synthetic processes exist for these compounds (See Yong-Uk Kwon et al, *J. Org. Chem.* 2002, vl. 67, 3327-3338 "Facile syntheses of all possible diastereomers of conduritol and various derivatives of inositol stereoisomers in high enantiopurity from myo-inositol"), there are still difficulties to obtain these compounds or corresponding analogues.

As it is apparent from the above, any efficient process for producing functionalised spirolactam compounds in high yield, with various functionalities, introduced in a controlled and regioselective manner, would be a welcome contribution to the art and will open the door to a variety of biologically active compounds.

SUMMARY OF THE INVENTION

Starting from the compounds described in our application EP 04380104.2, we found a basic set of processes that allows the controlled synthesis of very stable, highly functionalised, spiro-fused azetidinones which are useful as intermediate compounds in the preparation of a variety of chemical structures, including, if necessary, by means of chemo-, loco-, regio-, diastero- and/or enantioselective processes.

In one aspect the invention provides a compound of formula I:

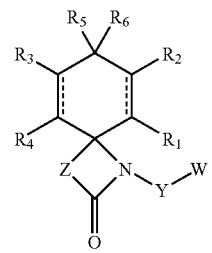

formula I wherein $R_1$, $R_2$, $R_3$, $R_4$ are each independently selected from H, OH or OPr;

$R_5$ and $R_6$ together are =O or $R_5$ is selected from H, OH, OPr and $R_6$ is selected from hydrogen, cyano, substituted or unsubstituted alkyl, substituted or unsubstituted cycloalkyl, substituted or unsubstituted alkenyl, substituted or unsubstituted alkynyl, substituted or unsubstituted aryl, substituted or unsubstituted heterocyclyl, with the proviso that at least one of $R_1$, $R_2$, $R_3$, $R_4$ or $R_5$ is OH or OPr;

Pr is an hydroxyl protecting group which can be the same or different on each of $R_1$, $R_2$, $R_3$, $R_4$ or $R_5$;

the dotted line represents a single or double bond, with the proviso that when both $R_1$ and $R_2$ or $R_3$ and $R_4$ are H then there is a double bond between the two C to which the H are linked;

Z is —(CRaRb)$_n$— wherein n is a number selected from 1, 2, 3 and Ra and Rb are each independently selected from hydrogen, substituted or unsubstituted alkyl, substituted or unsubstituted cycloalkyl, substituted or unsubstituted alkenyl, substituted or unsubstituted aryl, substituted or unsubstituted heterocyclyl, substituted or unsubstituted alkoxy, substituted or unsubstituted aryloxy, substituted or unsubstituted amino or halogen;

Y is selected from —O—, —S—, —N(RaRb)— or —C(O)—, wherein Ra and Rb are as previously defined and do not form a cyclic ring;

W is a group selected from substituted or unsubstituted arylalkyl, substituted or unsubstituted heterocyclylalkyl, substituted or unsubstituted alkenyl;

or a salt, complex or solvate thereof.

In one embodiment we prefer that n is 1. In this case Z is preferably —CH$_2$—. In another embodiment W is arylalkyl, preferably benzyl. In a further embodiment Y is preferably —O—.

The invention also provides for a process for the preparation of a compound according of formula I, which comprises in any order one or more steps selected from the group consisting of:

a) hydroxylation or dihydroxylation b) hydroxyl or carbonyl protection c) nucleophilic attack at the carbonyl group d) hydroxyl inversion applied to a compound of formula IV:

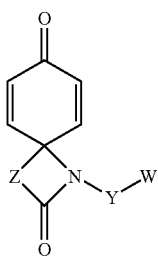

formula IV wherein Z, Y and W are as defined above.

DETAILED DESCRIPTION OF THE INVENTION

The invention provides compounds of formula I as above defined. In the compounds of formula I, the group Z gives rise to a ring of 4, 5 or 6 members. Substitution on position Z creates a stereogenic center that could induce selective functionalisation on the benzodienone moiety. In a preferred embodiment Z is —CH$_2$)$_n$—. Although rings of 5 or 6 are also comprised within the scope of the invention, in one embodiment the β-lactam ring (n=1) is preferred because of the further uses that can be given to such compounds.

The group Y in the compounds of formula I plays a role in the stability and conformation. In an embodiment Y is preferably —O—, although other atoms are not excluded as long as the final product is stable.

As we already mentioned the W group is important for the stabilization of the compound of formula I. Preferably it comprises unsaturated bonds or aromatic groups to increase the π interaction. Aralkyl groups and alkenyl groups are preferred since they give the best stability. In a particular embodiment, W is —CRaRb-Q or —SiRaRb-Q since the stability of the conformation is further improved by the presence of a —CRaRb— or a —SiRaRb— linker between Y and the substituent Q which has π (pi) interactions with the benzodienone moiety. The linker is preferably —CHRa—. In this case a stereogenic center is introduced which allows for the selectivity or specificity of any further reaction, distinguishing the two double bonds of the benzodienone. This will advantageously open the way to diastereo- and/or enantioselective synthesis in addition to the selection for one face which is explained below. Depending on the size of Ra it can also modulate the π (pi) interactions.

In one embodiment W is an aralkyl group. Among the aryl groups substituted or unsubstituted phenyl and naphthyl are preferred. Heterocyclylalkyl groups are also envisaged. Phenyl is the simplest substituent and gives good results.

In the above definition of compounds of formula (I) and in the description the following terms have the meaning indicated:

"Alkyl" refers to a straight or branched hydrocarbon chain radical consisting of carbon and hydrogen atoms, containing no saturation, having one to eight carbon atoms, and which is attached to the rest of the molecule by a single bond, e.g., methyl, ethyl, n-propyl, i-propyl, n-butyl, t-butyl, n-pentyl, etc. Alkyl radicals may be optionally substituted by one or more substituents independently selected from the group consisting of a halo, hydroxy, alkoxy, carboxy, cyano, carbonyl, acyl, alkoxycarbonyl, amino, nitro, mercapto and alkylthio.

"Alkoxy" refers to a radical of the formula —ORa where Ra is an alkyl radical as defined above, e.g., methoxy, ethoxy, propoxy, etc. "Aryloxy" refers to a radical of formula —ORb wherein Rb is an aryl radical as defined below.

"Amino" refers to a radical of the formula —NH$_2$, —NHRa, —NRaRb.

"Aryl" refers to a phenyl, naphthyl or anthracyl radical. The aryl radical may be optionally substituted by one or more substituents selected from the group consisting of hydroxy, mercapto, halo, alkyl, phenyl, alkoxy, haloalkyl, nitro, cyano, dialkylamino, aminoalkyl, acyl and alkoxycarbonyl, as defined herein.

"Aralkyl" refers to an aryl group linked to an alkyl group such as benzyl and phenethyl.

"Cycloalkyl" refers to a saturated carbocyclic ring having from 3 to 8 carbon atoms.

"Heterocycle" refers to a heterocyclyl radical. The heterocycle refers to a stable 3- to 15-membered ring which consists of carbon atoms and from one to five heteroatoms selected from the group consisting of nitrogen, oxygen, and sulfur, preferably a 4- to 8-membered ring with one or more heteroatoms, more preferably a 5- or 6-membered ring with one or more heteroatoms. For the purposes of this invention, the heterocycle may be a monocyclic, bicyclic or tricyclic ring system, which may include fused ring systems; and the nitrogen, carbon or sulfur atoms in the heterocyclyl radical may be optionally oxidised; the nitrogen atom may be optionally quaternized; and the heterocyclyl radical may be partially or fully saturated or aromatic. Examples of such heterocycles include, but are not limited to, azepines, benzimidazole, benzothiazole, furan, isothiazole, imidazole, indole, piperidine, piperazine, purine, quinoline, thiadiazole, tetrahydrofuran.

"Hydroxyl protecting group" refers to a group that blocks the OH function for further reactions. The hydroxyl protecting groups are well known in the art, representative protecting groups are silyl ethers such as trimethylsilyl ether, triethylsilyl ether, tert-butyldimethylsilyl ether, tert-butyldiphenylsilyl ether, tri-isopropylsilyl ether, diethylisopropylsilyl ether, thexyldimethylsilyl ether, triphenylsilyl ether, di-tert-butylmethylsilyl ether; alkyl ethers such as methyl ether, tert-butyl ether, benzyl ether, p-methoxybenzyl ether, 3,4-dimethoxybenzyl ether, trityl ether; allyl ether; alkoxymethyl ether such as methoxymethyl ether, 2-methoxyethoxymethyl ether, benzyloxymethyl ether, p-methoxybenzyloxymethyl ether, 2-(trimethylsilyl)ethoxymethyl ether; tetrahydropyranyl and related ethers; methylthiomethyl ether; Esters such as acetate ester, benzoate ester; pivalate ester; methoxyacetate ester; chloroacetate ester; levulinate ester; Carbonates such as benzyl carbonate, p-nitrobenzyl carbonate, tert-butyl carbonate, 2,2,2-trichloroethyl carbonate, 2-(trimethylsilyl)ethyl carbonate, allyl carbonate. Additional examples of hydroxyl protecting groups can be found in reference books such as Greene and Wuts' "Protective Groups in Organic Synthesis", John Wiley & Sons, Inc., New York, 1999.

References herein to substituted groups in the compounds of the present invention refer to the specified moiety that may be substituted at one or more available positions by one or more suitable groups, e.g., halogen such as fluoro, chloro, bromo and iodo; cyano; hydroxyl; nitro; azido; alkanoyl such as a C1-6 alkanoyl group such as acyl and the like; carboxamido; alkyl groups including those groups having 1 to about 12 carbon atoms or from 1 to about 6 carbon atoms and more preferably 1-3 carbon atoms; alkenyl and alkynyl groups including groups having one or more unsaturated linkages and from 2 to about 12 carbon or from 2 to about 6 carbon atoms; alkoxy groups having one or more oxygen linkages and from 1 to about 12 carbon atoms or 1 to about 6 carbon atoms; aryloxy such as phenoxy; alkylthio groups including those moieties having one or more thioether linkages and from 1 to about 12 carbon atoms or from 1 to about 6 carbon atoms; alkylsulfinyl groups including those moieties having one or more sulfinyl linkages and from 1 to about 12 carbon atoms or from 1 to about 6 carbon atoms; alkylsulfonyl groups including those moieties having one or more sulfonyl linkages and from 1 to about 12 carbon atoms or from 1 to about 6 carbon atoms; aminoalkyl groups such as groups having one or more N atoms and from 1 to about 12 carbon atoms or from 1 to about 6 carbon atoms; carbocylic aryl having 6 or more carbons, particularly phenyl or naphthyl and aralkyl such as benzyl. Unless otherwise indicated, an optionally substituted group may have a substituent at each substitutable position of the group, and each substitution is independent of the other.

In our copending application, EP04380104.2, which is incorporated herein by reference in its entirety, we describe new compounds having a formula IV and processes for their obtention:

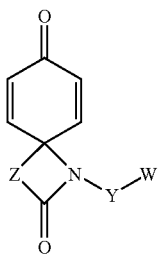

formula IV wherein Z is —CRaRb)$_n$— wherein n is a number selected from 1, 2, 3 and Ra and Rb are each independently selected from hydrogen, substituted or unsubstituted alkyl, substituted or unsubstituted cycloalkyl, substituted or unsubstituted alkenyl, substituted or unsubstituted aryl, substituted or unsubstituted heterocyclyl, substituted or unsubstituted alkoxy, substituted or unsubstituted aryloxy, substituted or unsubstituted amino, or halogen;

Y is selected from —O—, —S—, —N(RaRb)— or —C(O)—, wherein Ra and Rb are as previously defined and do not form a cyclic ring;

and W is a group with sufficient electronic density to stabilize the compound through π (pi) interactions with the benzodienone moiety, preferably a group having unsaturated bonds or aromatic groups, more preferably it is selected from substituted or unsubstituted arylalkyl, substituted or unsubstituted heterocyclylalkyl, substituted or unsubstituted alkenyl.

These compounds are remarkably stable due to π interactions between the W group and the benzodienone moiety. Additionally these compounds adopt a preferential conformation in which the W group blocks one of the faces of the benzodienone (hereinafter the β face) and is "fixed" there by the π interactions, directing further reactions to the free face of the benzodienone moeity (hereinafter the α face).

Taking advantage of this, we have now found that starting from these compounds it is possible to regioselectively hydroxylate, functionalise and protect the different positions of the benzodienone group, to give a broad range of stable compounds having the desired functionality and protection at each of the 5 available positions. These highly functionalised compounds are useful as building blocks for a wide variety of bioactive compounds.

If only one hydroxy group is desired, it can be introduced regioselectively for example via formation of the cyanhydrine on the carbonyl group, the hydroboration or hydrosililation of one of the double bonds (via the α face), then oxidation and final treatment with acid or AgF:

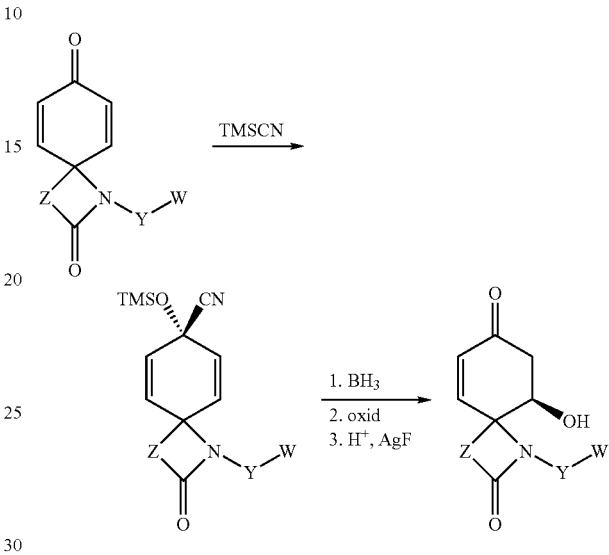

Other alternatives procedures are possible. Significantly, the hydroxylation takes place via one face of the dienone only. The hydroxyl group can then be protected with any desired hydroxyl protecting group such as those listed above.

In another embodiment of the invention we provide for the diastereoselective dihydroxylation of one of the double bonds of the benzodienone moiety. This is a surprising result, in view of the expected poor reactivity of the structure of formula IV, due to the highly deactivated double bonds. Additionally, contrary to what is expected, the dihydroxylation takes place regioselectively, only via the α face:

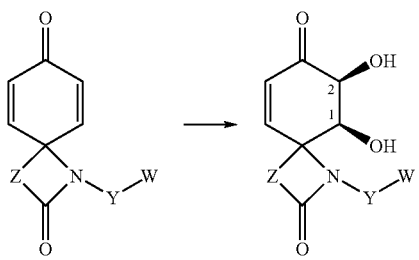

This oxidation occurs readily under mild conditions, such as using $OsO_4$ in a polar solvent, for example a mixture of water an ketone, in the presence of an amine such as N-methylmorpholine N-oxide. Alternative oxidation systems will be readily apparent to the person skilled in the are and can be found in standard references for organic synthesis such as Noyori, R. "Asymmetric catalysis in organic synthesis", John Wiley and Sons, Inc. (1994) or Ojima, I. "Catalytic asymmetric synthesis VCH, (1993)

In another aspect of the invention we have found that the dihydroxylated compound can be selectively protected.

Indeed, when carrying out a protection such as with Cl-TBDMS we found that the hydroxyl at position 2 reacted until being completely protected, and only then the OH at position 1 is protected.

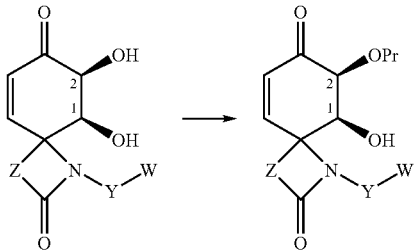

Without being bound by theory we believe that this is due to the existence of C—H π interactions between the H at position 2 and the W group. This means that the —OH at position 2 is in an equatorial conformation, more reactive, while the —OH at position 1 is in an axial conformation, less reactive. This allows the selective reaction of one position with respect to the other.

Therefore, both the facial selection (α versus β) when carrying out the hydroxylation, and the different reactivity of positions 1 and 2, due to the particular conformations generated by the presence of the W group and its interactions with the rest of the molecule, allows for a fine tuned control of the functionalisation of the molecule.

The two hydroxy groups can be protected with the same protecting group as explained above, or with different protecting groups, first protecting the position 2 and then the position 1:

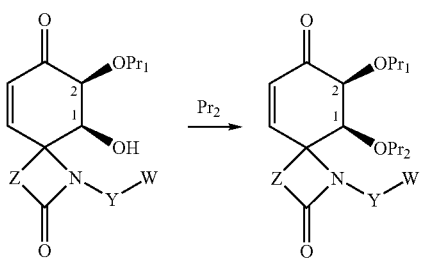

To introduce the hydroxyl protecting groups standard procedures can be used, such as those described in Greene and Wuts' "Protective Groups in Organic Synthesis", John Wiley & Sons, Inc., New York, 1999 or Kocienski, P. J. "Protecting Groups", 3$^{rd}$ Ed. Thieme Chemistry, 2003.

In another embodiment the carbonyl group can also be selectively functionalized for example by Nucleophilic addition. Importantly, the lactam group does not react instead because it has a Weinreb type of amide. Thus cyanides, organolithium compounds, Grignard's reagents, ketones among other can be easily added to introduce the desired functionality at this position. If an hydride is used then an hydroxy at position 3 is generated. Suitable procedures for this kind of reactions are known in the art and can be found for example in Fischer, A. et al *J. Org. Chem*, 1987, 52, 4464-4468 "Formation of 4-nitrocyclohexa-2,5-dienols by addition of organolithium reagents to 4-alkyl-4-nitrocyclohexa-2,5-dione"; Wipf et al., *Angew. Chem. Int. Ed. Engl.* 1997, 36, no. 7, 764-767; Fischer, A. et al., *Tetrahedron lett.*, 1980, 21, 701-704; Carreno, M. et al., *J. Org. Chem*, 1997, 62, 26, 9128-9137.

The additions can be done independently of the functionalisation of the other positions. If no other hydroxy groups are present:

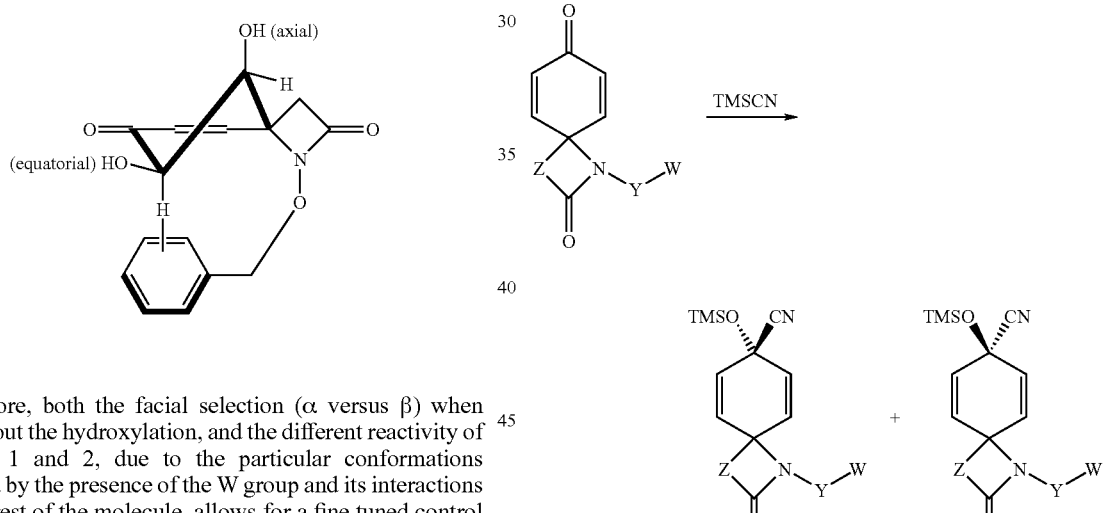

This reaction occurs with no stereoselectivity. The compounds can be in any case separated by resolution procedures know in the art, such as chromatography.

As an alternative to functionalisation, if desired the carbonyl group can be protected using know carbonyl protecting groups.

We have found that when the compound of formula IV is first dihydroxylated and then the addition to the carbonyl is carried out, complete stereoselectivity is achieved. Although not completely clear, it appears that this important stereoselectivity is due to stereoelectronic effects between positions 2 and 3, and to the above mentioned conformation at position 2. For example:

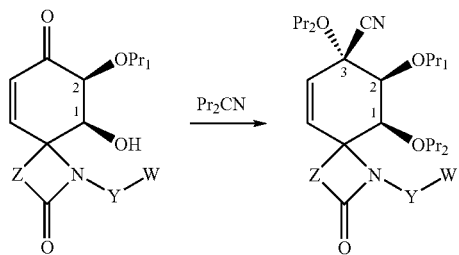

In this case the addition and the protection of the second hydroxyl group are carried out at the same time. Alternatively, only addition can take place.

In another aspect of the invention, the second double bond (positions 4 and 5) can also be stereoselectively hydroxylated. This occurs more readily when the carbonyl group at position 3 is present, we think because it allows the in situ generation of an allylic alcohol, which might indicate that it plays a role in the oxidation process. Thus, under mild conditions:

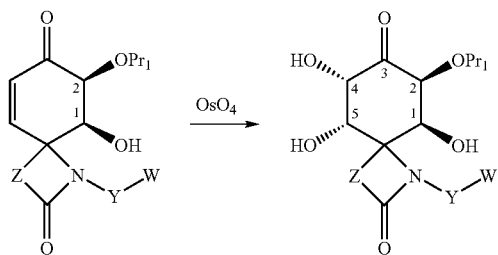

In this case the hydroxyl groups appear at the β face, we believe for stereoelectronic reasons. If a different stereochemistry is desired the appropriate oxidation or epimerization conditions can be selected. For example, under selective acidic or basic conditions the hydroxy at position 4 epimerizes. Alternatively hydroxyl inversions via the Mitsunobu type reaction, such as using DEAD, Ph$_3$P and an acid such as benzoic or p-nitrobenzoic acid, can be used. Frequently, the inversion via Mitsunobu needs protection of the other hydroxyl groups. Further details on the inversion via the Mitsunobu reaction can be found in Mitsunobu, O., *Synthesis*, 1, 1981; or Hughes, D. L., *Org. Reactions*, 1992, 42, 335.

If the carbonyl group has already been functionalized, then stronger oxidation conditions are needed, such as the use of RuCl$_3$ or similar systems:

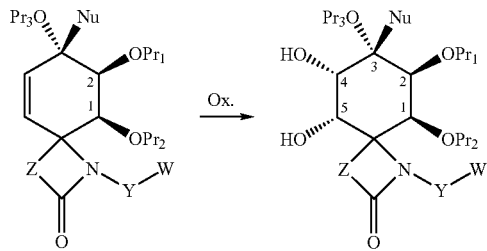

Complete orthogonal and complete regioselective protection can be achieved from here by introduction of a further protecting group:

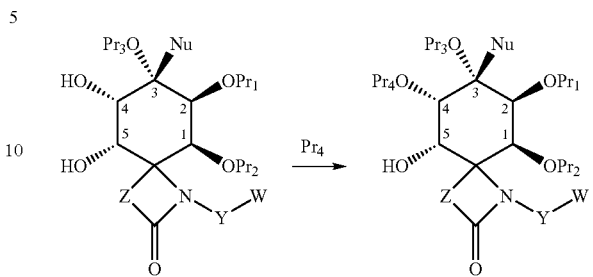

The presence of vicinal hydroxyl groups allows the simultaneous protection of two of them through the use of diol protecting groups if desired. Among the diol protecting groups that can be used we have O,O-acetals such as isopropylidene acetals (acetonides); cyclohexylidene and cyclopentylidene acetals; arylmethylene acetals; methylene acetals; diphenylmethylene acetals; 1,2-diacetals such as dispiroketal (dispoke) derivatives, cyclohexane-1,2-diacetals, butane-2,3-diacetals; silylene derivatives; 1,1,3,3-tetraisopropyldisiloxanylidene derivatives or N,O-acetals. Additional examples of diol protecting groups can be found in reference books such as Greene and Wuts' "Protective Groups in Organic Synthesis", John Wiley & Sons, Inc., New York, 1999.

As can be understood from the above and will be apparent to the person skilled in the art, due to the particular conformation and reactivity characteristics of the described compounds, a great number of possibilities can be achieved. It is important to point out that the obtained compounds of formula I will present a carefully crafted functionality at the different positions 1-5 and the desired stereochemistry. The introduction of different protecting groups opens the route to very selective further reactions by choosing the appropriate protection-deprotection strategies.

The process to obtain any of these compounds can be readily designed by starting from a compound of formula IV above and then applying a basic set of reactions selected from:

a) Hydroxylation or dihydroxylation: as above explained, using mild (such as OsO$_4$/N oxide amine) or strong systems (such as RuCl$_3$) depending on the position to be hydroxylated. Alternative systems are also envisaged.

b) Nucleophilic attack at the carbonyl group: for example with a carbanion on a sp, sp2 or sp3 C, the carbanion can be prepared or generated in situ; or with an hydride.

c) Hydroxyl inversion: as previously explained, for example through epimerization or inversion, for example in Mitsunobu conditions.

d) Hydroxyl or carbonyl protection: as explained above, using the same or different protecting groups in conditions as explained above.

Although each of these procedures is well known and the appropriate reagents can be selected by the person skilled in the art of organic synthesis, for example from those given in the references above, their application to the our structures gives unexpected results in terms of reactivity and selectivity.

The following scheme I illustrates some of the possibilities, when Z is —CH$_2$— and Y is O:

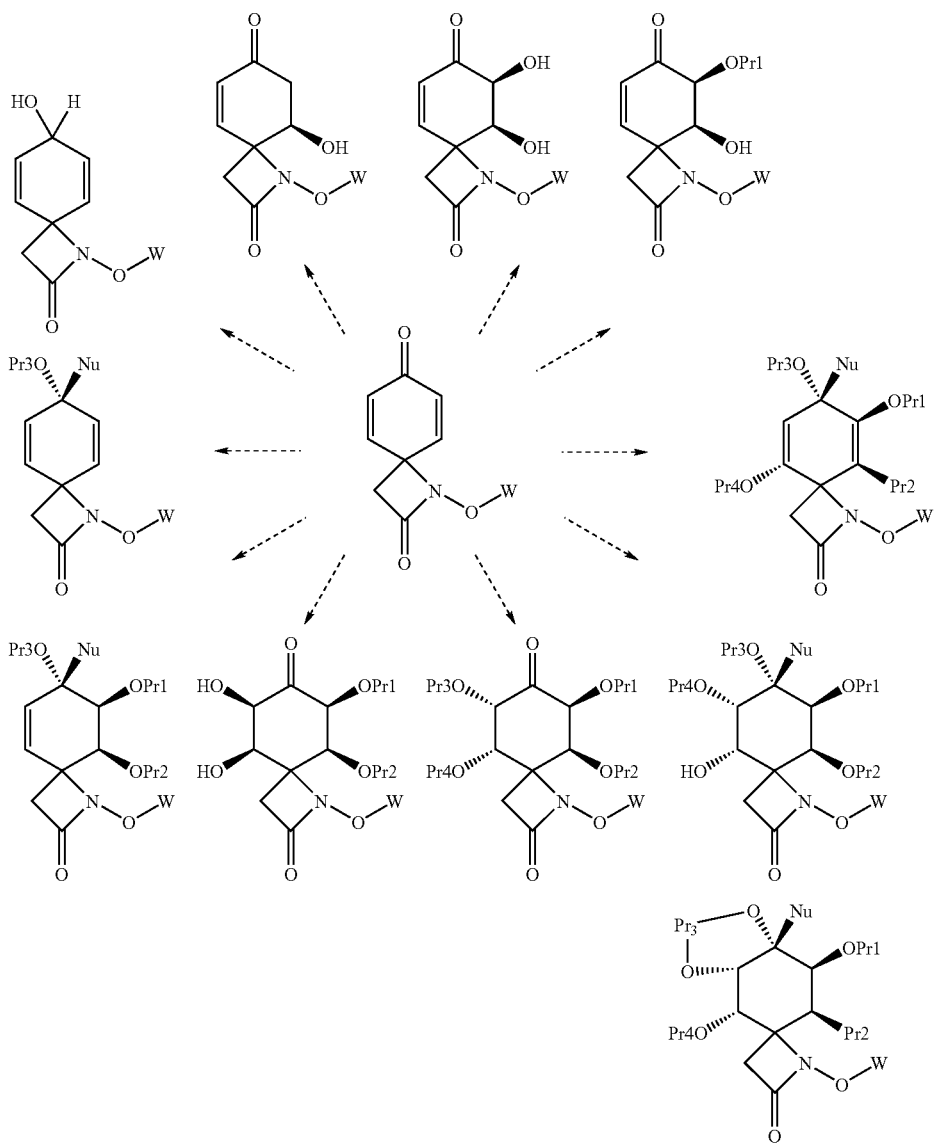

Scheme I

Mixtures of different diastereoisomers can be separated by conventional techniques. All the compounds will be obtained as racemic mixtures. However, if enantiopurity is desired, this can be achieved by introducing a chiral center in the W group as explained above, or using chiral reagents or catalysts. Therefore the compounds of the present invention represented by the above described formula (I) may include pure enantiomers depending on the presence of stereogenic centers or diastereoisomers. The single isomers, enantiomers or diastereoisomers and mixtures thereof fall within the scope of the present invention.

Unless otherwise stated, the compounds of the invention are also meant to include compounds which differ only in the presence of one or more isotopically enriched atoms. For example, compounds having the present structures except for the replacement of a hydrogen by a deuterium or tritium, or the replacement of a carbon by a $^{13}C$— or $^{14}C$-enriched carbon or $^{15}N$-enriched nitrogen are within the scope of this invention.

Salts of compounds of the invention are synthesized from the parent compound which contains a basic or acidic moiety by conventional chemical methods. Generally, such salts are, for example, prepared by reacting the free acid or base forms of these compounds with a stoichiometric amount of the appropriate base or acid in water or in an organic solvent or in a mixture of the two. Generally, nonaqueous media like ether, ethyl acetate, ethanol, isopropanol or acetonitrile are preferred. Examples of the acid addition salts include mineral acid addition salts such as, for example, hydrochloride, hydrobromide, hydroiodide, sulphate, nitrate, phosphate, and organic acid addition salts such as, for example, acetate, maleate, fumarate, citrate, oxalate, succinate, tartrate, malate, mandelate, methanesulphonate and p-toluenesulphonate.

The compounds of the invention may be in crystalline form either as free compounds or as solvates (e.g. hydrates) and it is intended that both forms are within the scope of the present invention. Methods of solvation are generally known within the art.

The invention will be further illustrated by means of examples.

EXAMPLES

General Methods and Materials

All reactions described below were carried out under argon atmosphere unless otherwise noted. The solvents used were distilled and dried under argon atmosphere before use. All starting materials were purchased commercially (Aldrich, Fluka and Merck) and used without further purification. Flash Chromatography was executed on columns loaded with 230-400 mesh silica gel Merck. TLC was carried out on silica gel Merck (Kieselgel 60F-254).

Melting points (mp) were determined on a Reichert Microscopic Hot-Stage and are uncorrected. $^1$H and $^{13}$C NMR spectra were measured on a Varian Gemini-200 and a Varian Inova-300 spectrometer with $(CH_3)_4Si$ as an internal reference and $CDCl_3$ as solvent unless otherwise noted. Both $^1$H and $^{13}$C NMR spectral data are reported in parts per million (δ) relative to residual sign of the solvent ($CDCl_3$, 7.26 ppm and 77.0 ppm for $^1$H and $^{13}$C NMR, respectively). $^1$H and $^{13}$C NMR designations are: s (singlete); s br. (broad singlete); d (doublete); t (triplete); q (quartete); m (multiplete). Infrared (IR) spectra were record on a Perkin-Elmer FT-IR spectrometer. UV spectra were record on a Perkin-Elmer 402 spectrometer. Low-resolution mass (LRMS) spectra were obtained on a Hewlett Packard 5973 MSD spectrometer with a direct inlet system (EI) at 70 eV. Microanalytical data (E.A.) were obtained on a Perkin-Elmer 240C and Heraus CHN—O instruments at the Instrumental Analysis Department of Instituto de Química Orgánica General (C.S.I.C.).

The compounds below are nominated as derivatives of 1-azaspiro[3.5]nonan-2-one and numerated following the numeration described below.

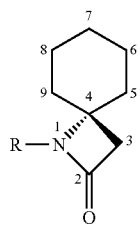

Example 1

Preparation of rac-(4R,5S,6S)-1-benzyloxy-5,6-dihidroxy-1-azaspiro[3,5]nona-8-ene-2,7-dione (2)

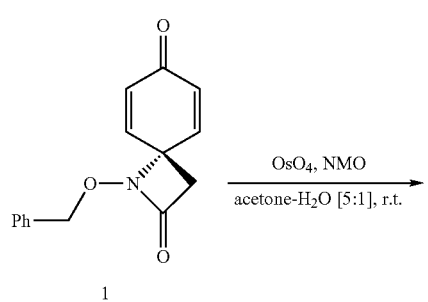

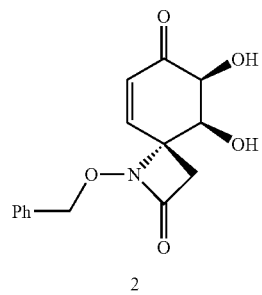

To a solution of meso-1-benzyloxy-1-azaspiro[3.5]nona-5,8-diene-2,7-dione (1) (804 mg, 3.150 mmol) in acetone (12 ml) was added sequentially at room temperature $H_2O$ (2.4 ml), N-methylmorpholine N-oxide (812 mg, 6.930 mmol) and osmium tetroxide (2.37 ml, 2.5 wt. % solution in 2-methyl-2-propanol, 0.189 mmol). The resulting mixture was stirred at room temperature until the reaction was complete (1 h, TLC monitoring, AcOEt), and then quenched with 10% aqueous $Na_2S_2O_3$ solution (3 ml). After 20 min, the mixture was extracted with AcOEt (5×6 ml). The combined organic extracts were dried over $Na_2SO_4$, filtered and concentrated under reduced pressure. The residue was purified by silica gel column chromatography (hexane-AcOEt, 3:2) to give rac-(4R,5S,6S)-1-benzyloxy-5,6-dihydroxy-1-azaspiro[3.5]nona-8-ene-2,7-dione (2) as a white solid (419 mg, 46%).

Rf=0.47 (TLC, AcOEt); yield, 46%; white solid; $^1$H-NMR (200 MHz, $CD_3OD$): δ 7.56 (5H, s, Ph), 6.69 (1H, part A syst. AB, $J_{9,8}$=10.1 Hz, H-9), 6.65 (1H, part B syst. AB, $J_{8,9}$=10.1 Hz, H-8), 5.19 (1H, part A syst. AB, J=11.2 Hz, $OCH_2Ph$), 5.14 (1H, part B syst. AB, J=11.2 Hz, $OCH_2Ph$), 4.56 (1H, d, J=2.9 Hz, H-6), 4.31 (1H, m, H-5), 3.32 (1H, part A syst. AB, J=14.4 Hz, H-3), 2.93 (1H, part B syst. AB, J=14.4, H-3); $^{13}$C-NMR (75 MHz, $CD_3OD$): δ 199.0, 167.0, 146.8, 136.7, 131.2, 131.1, 130.1, 80.9, 76.1, 74.2, 67.3, 43.4; IR (KBr): ν 3429, 1772, 1692, 1631, 1450, 1382, 1053, 698 $cm^{-1}$; LRMS (API-ES$^+$): m/z 312 (M+Na)$^+$, 290 (M+H)$^+$.

Example 2

Preparation of rac-(4R,5S,6S)-1-benzyloxy-6-tert-butyldimethylsilyloxy-5-hydroxy-1-azaspiro[3.5]nona-8-ene-2,7-dione (3)

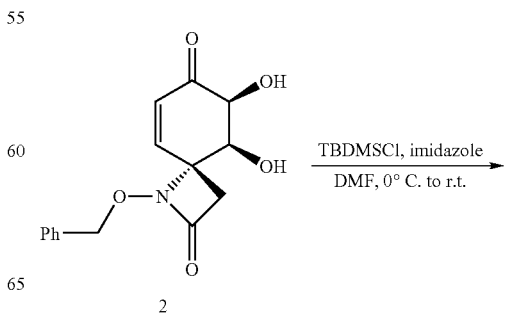

-continued

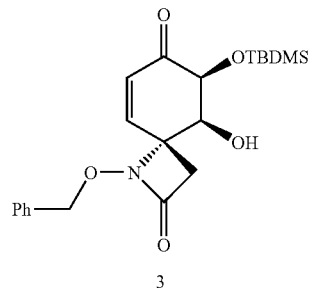

3

-continued

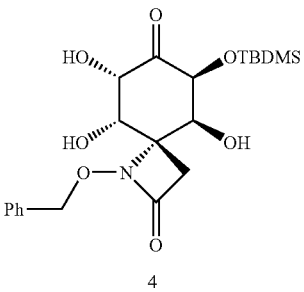

4

To a solution of rac-(4R,5S,6S)-1-benzyloxy-5,6-dihydroxy-1-azaspiro[3.5]nona-8-ene-2,7-dione (2) (123 mg, 0.425 mmol) and imidazole (35 mg, 0.510 mmol) in DMF (0.6 ml) was added at 0° C. a solution of tert-butyldimethylsilyl chloride (77 mg, 0.510 mmol) in DMF (1.2 ml). After 12 h at room temperature, the reaction was quenched with H$_2$O (3 ml) and the mixture extracted with AcOEt (3×5 ml). The combined extracts were washed with saturated aqueous CuSO$_4$ solution (2×10 ml) and brine (2×10 ml), dried over Na$_2$SO$_4$, filtered and concentrated under reduced pressure. The residue was purified by silica gel column chromatography (hexane-AcOEt, 5:2) to give rac-(4R,5S,6S)-1-benzyloxy-6-tert-butyldimethylsilyloxy-5-hydroxy-1-azaspiro[3.5]nona-8-ene-2,7-dione (3) as a white solid (133 mg, 78%).

R$_f$=0.56 (TLC, hexane-AcOEt, 1:1); yield, 78%; white solid; $^1$H-NMR (200 MHz, CDCl$_3$): δ 7.40-7.29 (5H, m, Ph), 6.24 (1H, part A syst. AB, J$_{9,8}$=10.1 Hz, H-9), 5.78 (1H, part B syst. AB, J$_{8,9}$=10.1 Hz, H-8), 5.00 (1H, part A syst. AB, J=11.4 Hz, OCH$_2$Ph), 4.87 (1H, part B syst. AB, J=11.4 Hz, OCH$_2$Ph), 4.36 (1H, d, J=2.7 Hz, H-6), 4.01 (1H, m, H-5), 3.25 (1H, part A syst. AB, J=14.6 Hz, CH$_2$), 2.63 (1H, part B syst. AB, J=14.6 Hz, CH$_2$), 2.56 (1H, d, J=3.8 Hz, OH), 0.85 (9H, s, C(CH$_3$)$_3$), 0.09 (3H, s, SiCH$_3$), 0.08 (3H, s, SiCH$_3$); $^{13}$C-NMR (75 MHz, CDCl$_3$): δ 195.4, 165.5, 145.2, 134.9, 129.6, 129.5, 129.3, 128.8, 79.3, 75.5, 71.7, 64.7, 41.9, 25.6, 18.1, 4.9, −5.3; IR (KBr): ν 3453, 2949, 2929, 2855, 1767, 1682, 1256, 1119, 1088, 980, 843, 782 cm$^{-1}$; LRMS (API-ES$^+$): m/z 829 (2M+Na)$^+$, 426 (M+Na)$^+$, 404 (M+H)$^+$.

To a stirred solution of rac-(4R,5S,6S)-1-benzyloxy-6-tert-butyldimethylsilyloxy-5-hydroxy-1-azaspiro[3.5]nona-8-ene-2,7-dione (3) (50 mg, 0.124 mmol) in acetone (0.45 ml) was added sequentially at room temperature H$_2$O (0.09 ml), N-methylmorpholine N-oxide (58 mg, 0.496 mmol) and osmium tetroxide (93 µl, 2.5 wt. % solution in 2-methyl-2-propanol, 7.4·10$^{-3}$ mmol). The resulting mixture was stirred at room temperature until the reaction was complete (18 h, TLC monitoring, hexane-AcOEt, 1:1), and then quenched with 10% aqueous Na$_2$S$_2$O$_3$ solution (20 drops). After 20 min, the mixture was filtered through silica gel with MeOH and concentrated under reduced pressure. The residue was purified by silica gel column chromatography (hexane-AcOEt, 2:1) to give rac-(4R,5S,6S,8S,9S)-1-benzyloxy-6-tert-butyldimethylsilyloxy-5,8,9-trihydroxy-1-azaspiro[3.5]nona-2,7-dione (4) as a white solid (26 mg, 48%).

R$_f$=0.46 (TLC, hexane-AcOEt, 1:1); yield, 48%; white solid; $^1$H-NMR (200 MHz, CDCl$_3$): δ 7.49-7.30 (5H, m, Ph), 5.11 (1H, part A syst. AB, J=10.6 Hz, OCH$_2$Ph), 5.05 (1H, part B syst. AB, J=10.6 Hz, OCH$_2$Ph), 4.68 (1H, dd, J=4.3, 3.7 Hz, H-8), 4.44-4.32 (2H, m, H-5 and H-6), 4.22 (1H, dd, J=1.8, 1.5 Hz, H-9), 3.48 (1H, d, J=4.3 Hz, HO—C(8)), 3.36 (1H, part A syst. AB, J=14.3 Hz, CH$_2$), 2.73 (1H, d, J=1.8 Hz, HO—C(9)), 2.45 (1H, part B syst. AB, J=14.3 Hz, CH$_2$), 2.28 (1H, s br, HO—C(5)), 0.85 (9H, s, C(CH$_3$)$_3$), 0.13 (3H, s, SiCH$_3$), 0.04 (3H, s, SiCH$_3$); $^{13}$C-NMR (75 MHz, CDCl$_3$): δ 204.8, 166.1, 135.1, 129.4, 129.0, 128.5, 78.9, 76.4, 75.5, 72.2, 67.4, 65.7, 37.5, 25.6, 18.0, −5.0, −5.3; IR (KBr): ν 3435, 2949, 2927, 2855, 1761, 1740, 1631, 1261, 1110, 1078, 837 cm$^{-1}$; LRMS (API-ES$^+$): m/z 897 (2M+Na)$^+$, 460 (M+Na)$^+$, 438 (M+H)$^+$.

Example 3

Preparation of rac-(4R,5S,6S,8S,9S)-1-benzyloxy-6-tert-butyldimethylsilyloxy-5,8,9-trihydroxy-1-azaspiro[3.5]nona-2,7-dione (4)

Example 4

Preparation of rac-(4R,5S,6S,8S,9S)-1-benzyloxy-6-tert-butyldimethylsilyloxy-5-hydroxy-8,9-dimethylmethylendioxy-1-azaspiro[3.5]nona-2,7-dione (5)

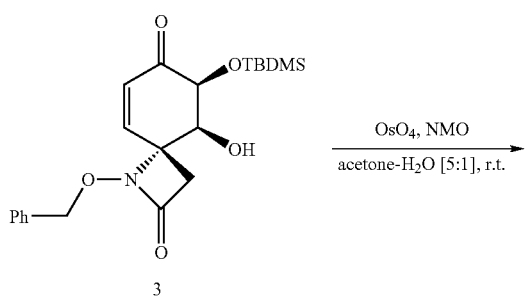

3

OsO$_4$, NMO
———————→
acetone-H$_2$O [5:1], r.t.

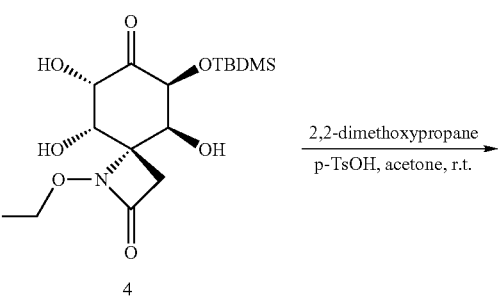

4

2,2-dimethoxypropane
———————→
p-TsOH, acetone, r.t.

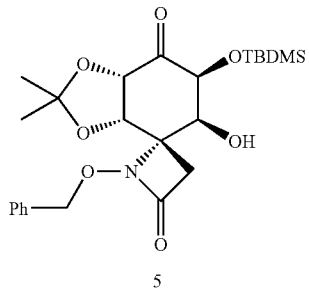

To a stirred solution of rac-(4R,5S,6S,8S,9S)-1-benzyloxy-6-tert-butyldimethylsilyloxy-5,8,9-trihydroxy-1-azaspiro[3.5]nona-2,7-dione (4) (50 mg, 0.115 mmol) and 2,2-dimethoxypropane (71 μl, 0.575 mmol) in dry acetone (0.5 ml) was added at room temperature catalytic amount of p-TsOH (1% mmol). The resulting mixture was stirred at room temperature for 18 h, then quenched with saturated aqueous Na$_2$CO$_3$ solution (1 ml) and extracted with AcOEt (3×2 ml). The combined organic extracts were washed with brine (3 ml), dried over Na$_2$SO$_4$, filtered and concentrated under reduced pressure. The residue was purified by silica gel column chromatography (hexane-AcOEt, 3:1) to give rac-4R,5S,6S,8S,9S)-1-benzyloxy-6-tert-butyldimethylsilyloxy-5-hydroxy-8,9-dimethylmethylendioxy-1-azaspiro[3.5]nona-2,7-dione (5) as a white solid (27 mg, 49%) and unreacted starting material (5) (13 mg, 24%).

R$_f$=0.77 (TLC, hexane-AcOEt, 1:1); yield, 49%; white solid; $^1$H-NMR (200 MHz, CDCl$_3$): δ 7.40-7.34 (5H, m, Ph), 5.05 (1H, part A syst. AB, J=10.2 Hz, OCH$_2$Ph), 5.02 (1H, part B syst. AB, J=10.2 Hz, OCH$_2$Ph), 4.84 (1H, d, J=5.4 Hz, H-8), 4.45 (1H, d, J=5.4 Hz, H-9), 4.39 (1H, d, J=2.7 Hz, H-6), 4.35 (1H, dd, J=5.9, 2.7 Hz, H-5), 3.45 (1H, part A syst. AB, J=14.2 Hz, CH$_2$), 2.56 (1H, d, J=5.9 Hz, OH), 2.48 (1H, part B syst. AB, J=14.2 Hz, CH$_2$), 0.86 (9H, s, C(CH$_3$)$_3$), 0.11 (3H, s, SiCH$_3$), 0.06 (3H, s, SiCH$_3$); $^{13}$C-NMR (75 MHz, CDCl$_3$): δ 203.6, 165.8, 135.0, 129.3, 128.9, 128.5, 111.3, 79.8, 79.0, 78.9, 77.7, 66.1, 65.4, 39.4, 26.9, 25.9, 25.5, 18.0, −5.1, −5.3; IR (KBr): ν 3434, 2930, 2855, 1764, 1739, 1628, 1453, 1384, 1255, 1225, 1111, 1086, 898, 832, 784 cm$^{-1}$; LRMS (API-ES$^+$): m/z 977 (2M+Na)$^+$, 500 (M+Na)$^+$, 478 (M+H)$^+$.

Example 5

Preparation of rac-(4R,5S,6S)-1-benzyloxy-6-tert-butyldimethylsilyloxy-5-trimethylsilyloxy-1-azaspiro[3.5]nona-8-ene-2,7-dione (6)

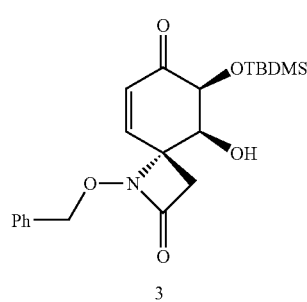

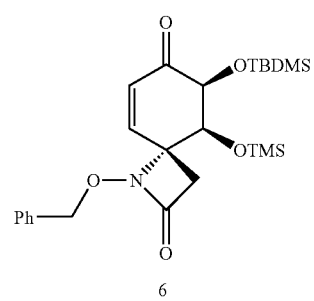

A solution of rac-(4R,5S,6S)-1-benzyloxy-6-tert-butyldimethylsilyloxy-5-hydroxy-1-azaspiro[3.5]nona-8-ene-2,7-dione (3) (130 mg, 0.322 mmol) in 1-trimethylsilylimidazole (0.5 ml, 3.220 mmol) was stirred at room temperature for 16 h. The reaction was quenched with Na$_2$PO$_4$ 0.1 M buffer (2 ml) and the mixture extracted with AcOEt (3×4 ml). The combined extracts were washed with saturated aqueous CuSO$_4$ solution (1×8 ml) and brine (2×8 ml), dried over Na$_2$SO$_4$, filtered and concentrated under reduced pressure. The residue was purified by silica gel column chromatography (hexane-AcOEt, 5:1) to give rac-(4R,5S,6S)-1-benzyloxy-6-tert-butyldimethylsilyloxy-5-trimethylsilyloxy-1-azaspiro[3.5]nona-8-ene-2,7-dione (6) as a white solid (100 mg, 65%).

R$_f$=0.50 (TLC, hexane-AcOEt, 3:1); yield, 65%; white solid; $^1$H-NMR (200 MHz, CDCl$_3$): δ 7.42-7.28 (5H, m, Ph), 6.09 (1H, part A syst. AB, J$_{9,8}$=10.3 Hz, H-9), 5.68 (1H, part B syst. AB, J$_{8,9}$=10.3 Hz, H-8), 4.98 (1H, part A syst. AB, J=11.6 Hz, OCH$_2$Ph), 4.84 (1H, part B syst. AB, J=11.6 Hz, OCH$_2$Ph), 4.13 (2H, d, J=2.4 Hz, H-5 and H-6), 3.40 (1H, m, CH$_2$), 2.47 (1H, d, J=14.2 Hz, CH$_2$), 0.79 (9H, s, C(CH$_3$)$_3$), 0.16 (9H, s, Si(CH$_3$)$_3$), 0.08 (3H, s, SiCH$_3$), 0.00 (3H, s, SiCH$_3$); LRMS (API-ES$^+$): m/z 973 (2M+Na)$^+$, 498 (M+Na)$^+$, 476 (M+H)$^+$; LRMS (EI): m/z 475 (M$^+$, 3), 460 (2), 418 (21), 384 (5), 368 (4), 354 (4), 340 (4), 324 (3), 309 (13), 269 (43), 179 (24), 147 (34), 91 (100), 73 (57).

Example 6

Preparation of rac-(4R,5S,6S,7S)-1-benzyloxy-6-tert-butyldimethylsilyloxy-7-cyano-5,7-bis(trimethylsilyloxy)-1-azaspiro[3.5]nona-8-ene-2-one (7)

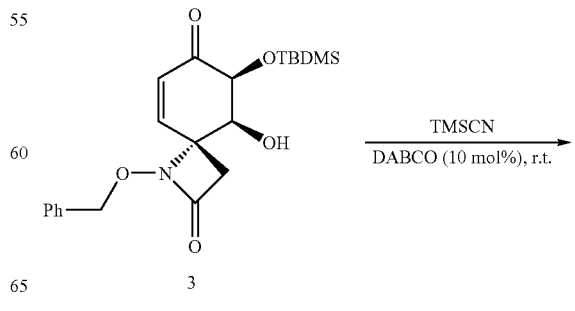

-continued

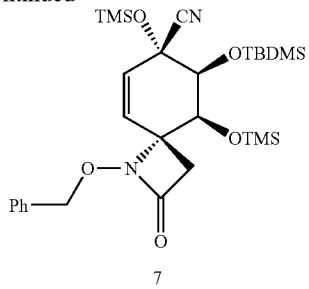

7

-continued

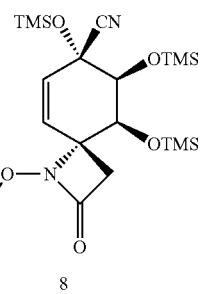

8

To a mixture of rac-(4R,5S,6S)-1-benzyloxy-6-tert-butyldimethylsilyloxy-1-azaspiro[3.5]nona-8-ene-2,7-dione (3) (200 mg, 0.496 mmol) and trimethylsilyl cyanide (607 μl, 4.460 mmol) at room temperature (cooled with water bath) was slowly added DABCO (6 mg, 0.050 mmol). The mixture was stirred at room temperature for 14 h and then concentrated under reduced pressure. The residue was purified by silica gel column chromatography (hexane-AcOEt, 5:1) to give rac-(4R,5S,6S,7S)-1-benzyloxy-6-tert-butyldimethylsilyloxy-7-cyano-5,7-bis(trimethylsilyloxy)-1-azaspiro[3.5]nona-8-ene-2-one (7) as a orange solid (254 mg, 89%).

Rf=0.61 (TLC, hexane-AcOEt, 3:1); yield, 89%; orange solid; $^1$H-NMR (300 MHz, CDCl$_3$): δ 7.37 (5H, s, Ph), 5.72 (1H, d, J=10.0 Hz, H-9), 5.21 (1H, dd, J=10.0, 1.9 Hz, H-8), 4.96 (1H, part A syst. AB, J=11.6 Hz, OCH$_2$Ph), 4.82 (1H, part B syst. AB, J=11.6 Hz, OCH$_2$Ph), 4.49 (1H, d, J=1.5 Hz, H-6), 4.10 (1H, t, J=1.9, 1.5 Hz, H-5), 3.32 (1H, part A syst. AB, J=13.8 Hz, H-3), 2.26 (1H, part A syst. AB, J=13.8 Hz, H-3), 0.80 (9H, s, C(CH$_3$)$_3$), 0.28 (9H, s, Si(CH$_3$)$_3$), 0.20 (9H, s, Si(CH$_3$)$_3$), 0.09 (3H, s, SiCH$_3$), 0.04 (3H, s, SiCH$_3$); $^{13}$C-NMR (75 MHz, CDCl$_3$): δ 165.7, 135.6, 132.6, 129.3, 128.8, 128.7, 126.9, 119.7, 78.8, 78.6, 69.8, 67.0, 65.6, 40.6, 25.8, 18.2, 1.4, 0.2, −4.1, −4.6, −7.0; IR (NaCl, CCl$_4$): ν 2957, 2891, 2855, 1785, 1255, 1101, 878, 843, 753 cm$^{-1}$; LRMS (API-ES$^+$): m/z 1171 (2M+Na)$^+$, 598 (M+Na)$^+$, 575 (M+H)$^+$.

To a mixture of rac-(4R,5S,6S)-1-benzyloxy-5,6-dihydroxy-1-azaspiro[3.5]nona-8-ene-2,7-dione (2) (44 mg, 0.152 mmol) and trimethylsilyl cyanide (186 μl, 1.368 mmol) at room temperature (cooled with water bath) was slowly added DABCO (2 mg, 0.015 mmol). The mixture was stirred at room temperature for 14 h and then concentrated under reduced pressure. The residue was purified by silica gel column chromatography (hexane-AcOEt, 5:1) to give rac-(4R,5S,6S,7S)-1-benzyloxy-7-cyano-5,6,7-tris(trimethylsilyloxy)-1-azaspiro[3.5]nona-8-ene-2-one (8) as a yellow solid (51 mg, 62%).

R$_f$=0.50 (TLC, hexane-AcOEt, 3:1); yield, 62%; yellow solid; $^1$H-NMR (200 MHz, CDCl$_3$): δ 7.37 (5H, s br, Ph), 5.33-5.20 (2H, m, H-8 and H-9), 4.96 (1H, part A syst. AB, J=11.6 Hz, OCH$_2$Ph), 4.81 (1H, part B syst. AB, J=11.6 Hz, OCH$_2$Ph), 4.41 (1H, d, J=1.5 Hz, H-5 or H-6), 4.08 (1H, t, J=1.5 Hz, H-6 or H-5), 3.27 (1H, part A syst. AB, J=14.1 Hz, CH$_2$), 2.27 (1H, part B syst. AB, J=14.1 Hz, CH$_2$), 0.27 (9H, s, Si(CH$_3$)$_3$), 0.20 (9H, s, Si(CH$_3$)$_3$), 0.08 (9H, s, Si(CH$_3$)$_3$); $^{13}$C-NMR (75 MHz, CDCl$_3$): δ 165.9, 135.6, 132.8, 129.2, 128.8, 128.7, 126.7, 119.6, 78.8, 78.4, 69.4, 66.8, 65.5, 40.3, 1.3, 0.4, 0.2; IR (NaCl, CCl$_4$): 3391, 2958, 2898, 2222, 1785, 1455, 1400, 1253, 1168, 1104, 1030, 880, 843, 752 cm$^{-1}$; LRMS (API-ES$^+$): m/z 1087 (2M+Na)$^+$, 555 (M+Na)$^+$, 533 (M+H)$^+$.

Example 7

Preparation of rac-(4R,5S,6S,7S)-1-benzyloxy-7-cyano-5,6,7-tris(trimethylsilyloxy)-1-azaspiro[3.5]nona-8-ene-2-one (8)

Example 8

Preparation of rac-(4R,5S,6S,7S)-1-benzyloxy-7-cyano-6-tert-butyldimethylsilyloxy-5,7-bis(methoxycarbonyloxy)-1-azaspiro[3.5]nona-8-ene-2-one (9)

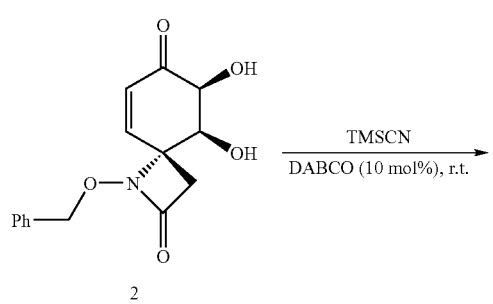

2

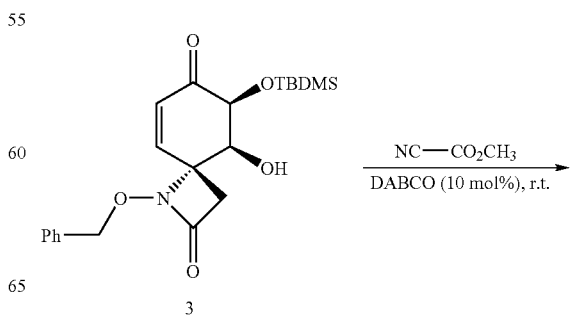

3

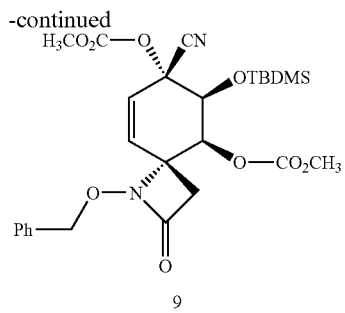

9

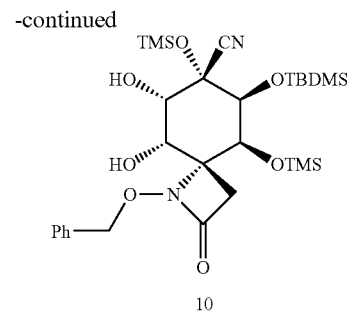

10

To a mixture of rac-(4R,5S,6S)-1-benzyloxy-6-tert-butyldimethylsilyloxy-5-hydroxy-1-azaspiro[3.5]nona-8-ene-2,7-dione (3) (95 mg, 0.235 mmol) and methylcyanoformate (169 μl, 2.115 mmol) was added at room temperature DABCO (3 mg, 0.023 mmol). The mixture was stirred at room temperature for 14 h and then concentrated under reduced pressure. The residue was triturated with Et$_2$O, filtered and the solvent was evaporated under reduced pressure to give rac-(4R,5S,6S,7S)-1-benzyloxy-7-cyano-6-tert-butyldimethylsilyloxy-5,7-bis(methoxycarbonyloxy)-1-azaspiro[3.5]nona-8-ene-2-one (9) as a brown oil (110 mg, 86%), was used in the next reaction without further purification.

$R_f$=0.65 (TLC, hexane-AcOEt, 1:1); yield, 86%; brown oil; $^1$H-NMR (200 MHz, CDCl$_3$): δ 7.39 (5H, s br, Ph), 5.73 (1H, dd, J=10.3, 2.0 Hz, H-8 or H-9), 5.46 (1H, d, J=10.3 Hz, H-9 or H-8), 5.40 (1H, d, J=1.8 Hz, H-5 or H-6), 4.95 (1H, part A syst. AB, J=11.5 Hz, OC$\underline{H}_2$Ph), 4.87 (1H, part B syst. AB, J=11.5 Hz, OC$\underline{H}_2$Ph), 4.77 (1H, dd, J=2.0, 1.8 Hz, H-6 or H-5), 3.85 (3H, s, OCH$_3$), 3.84 (3H, s, OCH$_3$), 3.29 (1H, part A syst. AB, J=14.4 Hz, CH$_2$), 2.44 (1H, part B syst. AB, J=14.4 Hz, CH$_2$), 0.79 (9H, s, C(CH$_3$)$_3$), 0.07 (3H, s, SiCH$_3$), 0.04 (3H, s, SiCH$_3$); $^{13}$C-NMR (75 MHz, CDCl$_3$): δ 165.5, 154.2, 152.9, 135.2, 133.9, 129.4, 129.3, 129.0, 128.9, 123.2, 115.1, 79.1, 72.5, 72.3, 70.9, 63.1, 55.7, 55.5, 41.7, 25.5, 25.1, 17.9, −4.5, −5.5; IR (NaCl, CCl$_4$): 3355, 2958, 2927, 2855, 2233, 1786, 1763, 1442, 1274, 1255, 1155, 1050, 834, 783 cm$^{-1}$; LRMS (API-ES$^+$): m/z 1115 (2M+Na)$^+$, 569 (M+Na)$^+$, (M+H)$^+$; LRMS (EI): m/z 546 (M$^+$, 2), 489 (5), 455 (1), 413 (3), 337 (18), 323 (4), 295 (17), 216 (10), 190 (17), 133 (16), 91 (100).

To a solution of rac-(4R,5S,6S,7S)-1-benzyloxy-6-tert-butyldimethylsilyloxy-7-cyano-5,7-bis(trimethylsilyloxy)-1-azaspiro[3.5]nona-8-ene-2-one (7) (100 mg, 0.174 mmol) in AcOEt (1 ml) and CH$_3$CN (1 ml) was added at 0° C. with vigorous stirring a solution of ruthenium (III) chloride hydrate (9 mg, 0.043 mmol) and sodium periodate (71 mg, 0.331 mmol) in H$_2$O (0.35 ml). After 5 min the reaction the mixture was quenched with saturated aqueous sodium hydrogensulfite solution (2 ml) and extracted with AcOEt (3×2 ml). The combined organic extracts were dried over MgSO$_4$, filtered and concentrated under reduced pressure. The residue was purified by silica gel column chromatography (hexane-AcOEt, 5:1) to give rac-(4R,5S,6S,7S,8S,9S)-1-benzyloxy-6-tert-butyldimethylsilyloxy-7-cyano-8,9-dihydroxy-5,7-bis(trimethylsilyloxy)-1-azaspiro[3.5]nona-2-one (10) as a white solid (73 mg, 69%).

Rf=0.33 (TLC, hexane-AcOEt, 3:1); yield, 69%; white solid; $^1$H-NMR (200 MHz, CDCl$_3$): δ 7.47-7.33 (5H, m, Ph), 5.21 (1H, part A syst. AB, J=10.1 Hz, OC$\underline{H}_2$Ph), 5.02 (1H, part B syst. AB, J=10.1 Hz, OC$\underline{H}_2$Ph), 4.74 (1H, d, J=2.1 Hz, H-8 or H-7), 4.10 (1H, d, J=2.1 Hz, H-7 or H-8), 3.92 (1H, m, H-6 or H-5), 3.83 (1H, m, H-5 or H-6), 3.27 (1H, part A syst. AB, J=14.0 Hz, H-3), 3.27 (1H, s, OH), 2.15 (1H, part B syst. AB, J=14.0 Hz, H-3), 2.01 (1H, s, OH), 0.86 (9H, s, C(CH$_3$)$_3$), 0.30 (9H, s, Si(CH$_3$)$_3$), 0.14 (3H, s, SiCH$_3$), 0.13 (9H, s, Si(CH$_3$)$_3$), 0.11 (3H, s, SiCH$_3$); $^{13}$C-NMR (50 MHz, CDCl$_3$): δ 166.0, 134.9, 128.9, 128.5, 119.3, 97.1, 78.9, 78.7, 74.8, 73.9, 70.9, 68.8, 65.2, 38.6, 26.1, 18.3, 1.8, 0.4, −3.8, −5.0; IR (KBr): ν 3434, 3028, 2957, 2927, 2898, 2855, 2152, 1762, 1630, 1253, 1169, 1107, 846, 740 cm$^{-1}$; LRMS (API-ES$^+$): m/z 1240 (2M+Na)$^+$, 631 (M+Na)$^+$, 609 (M+H)$^+$.

Example 9

Preparation of rac-(4R,5S,6S,7S,8S,9S)-1-benzyloxy-6-tert-butyldimethylsilyloxy-7-cyano-8,9-dihydroxy-5,7-bis(trimethylsilyloxy)-1-azaspiro[3.5]nona-2-one (10)

Example 10

Preparation of rac-(4R,5S,6S,7S,8S,9S)-1-benzyloxy-6,8-bis(tert-butyldimethylsilyloxy)-7-cyano-9-hydroxy-5,7-bis(trimethylsilyloxy)-1-azaspiro[3.5]nona-2,7-dione (11)

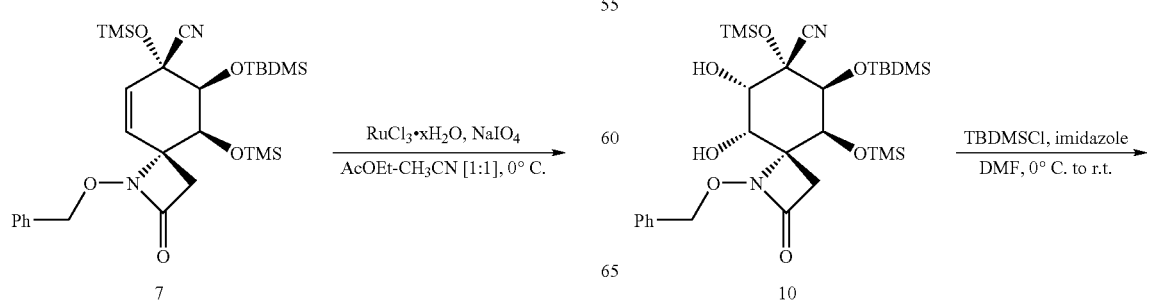

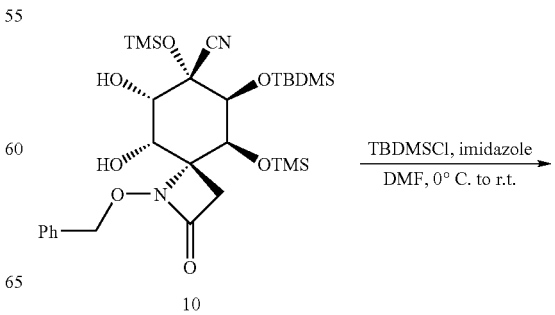

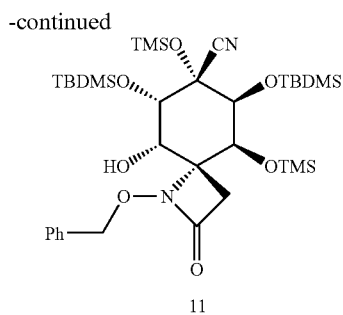

To a solution of rac-(4R,5S,6S,7S,8S,9S)-1-benzyloxy-6-tert-butyldimethylsilyloxy-7-cyano-8,9-dihydroxy-5,7-bis(trimethylsilyloxy)-1-azaspiro[3.5]nona-2,7-dione (10) (63 mg, 0.103 mmol) and imidazole (8 mg, 0.124 mmol) in DMF (0.25 ml) was added at 0° C. a solution of tert-butyldimethylsilyl chloride (19 mg, 0.124 mmol) in DMF (0.5 ml). After 16 h at room temperature, the reaction was quenched with $H_2O$ (2 ml) and the mixture extracted with AcOEt (3×4 ml). The combined extracts were washed with saturated aqueous $CuSO_4$ solution (2×8 ml) and brine (2×8 ml), dried over $Na_2SO_4$, filtered and concentrated under reduced pressure. The residue was purified by silica gel column chromatography (hexane-AcOEt, 5:1) to give rac-(4R,5S,6S,7S,8S,9S)-1-benzyloxy-6,8-bis(tert-butyldimethylsilyloxy)-7-cyano-9-hydroxy-5,7-bis(trimethylsilyloxy)-1-azaspiro[3.5]nona-2,7-dione (11) as a white solid (37 mg, 46%).

$R_f$=0.60 (TLC, hexane-AcOEt, 3:1); yield, 46%; white solid; $^1$H-NMR (200 MHz, $CO(CD_3)_2$): δ 7.54-7.42 (2H, m, Ph), 7.41-7.29 (3H, m, Ph), 5.26 (1H, part A syst. AB, J=10.2 Hz, $OCH_2Ph$), 5.06 (1H, part B syst. AB, J=10.2 Hz, $OCH_2Ph$), 4.82 (1H, d, J=2.4 Hz, H-5), 4.70 (1H, d, J=2.4 Hz, OH), 4.27 (1H, d, J=2.4 Hz, H-6), 4.16 (1H, m, H-9), 3.99 (1H, s br, H-8), 3.23 (1H, part A syst. AB, J=13.7 Hz, $CH_2$), 2.89 (1H, part B syst. AB, J=13.7 Hz, $CH_2$), 0.91 (18H, s, $C(CH_3)_3$), 0.19 (6H, s, $SiCH_3$), 0.18 (6H, s, $SiCH_3$), 0.11 (18H, s, $Si(CH_3)_3$).

Example 11

General Procedure for the Preparation of the Silylcyanohydrin 12a and 12b from the Spiro β-Lactams 1a and 1b, Respectively

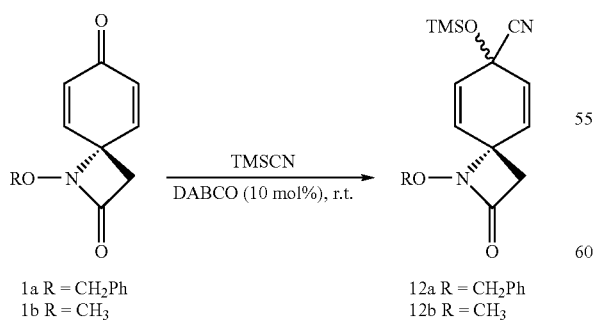

1a R = CH$_2$Ph
1b R = CH$_3$

12a R = CH$_2$Ph
12b R = CH$_3$

To a mixture of spiro β-lactams 1a-b (0.588 mmol) and trimethylsilyl cyanide (1.763 mmol) at room temperature (cooled with water bath) was slowly added DABCO (10 mol %). The mixture was stirred at room temperature until the disappearance of starting material by TLC (hexane-AcOEt, 1:1) was observed (the time required was 6 h for 1a and 24 h for 1b), and then concentrated under reduced pressure. The silylcyanohydrin 12a-b isolated by procedure could be used without further purification (the purification by silica gel column chromatography to give mixtures of silylcyanohydrin 12a-b and starting material 1a-b).

rac-(4R,7S) and (4R,7R)-1-benzyloxy-7-cyano-1-azaspiro[3.5]nona-5,8-diene-2-one (12a) $R_f$=0.64 (TLC, hexane-AcOEt, 1:1); yield, 88%; brown solid; $^1$H-NMR (200 MHz, $CDCl_3$): δ 7.37 (5H, m Ph), 7.35 (5H, m, Ph), 6.09 (2H, part AA' syst. AA'BB', $J_{5,6}$=10.0 Hz, $CH$=CHCO), 6.06 (2H, part AA' syst. AA'BB', $J_{5,6}$=10.1 Hz, CH=CHCO), 5.87 (2H, part BB' syst. AA'BB', $J_{6,5}$=10.1 Hz, CH=CHCO), 5.79 (2H, part BB' syst. AA'BB', $J_{6,5}$=10.1 Hz, CH=CHCO), 4.89 (2H, s, $OCH_2Ph$), 4.87 (2H, s, $OCH_2Ph$), 2.75 (2H, s, $CH_2$), 2.73 (2H, s, $CH_2$), 0.26 (9H, s, $Si(CH_3)_3$), 0.19 (9H, s, $Si(CH_3)_3$).

rac-(4R,7S) and 4R,7R)-1-methoxy-7-cyano-1-azaspiro[3.5]nona-5,8-diene-2-one (12b) $R_f$=0.61 (TLC, hexane-AcOEt, 1:2); yield, 64%; brown solid; $^1$H-NMR (200 MHz, $CDCl_3$): δ 6.26 (2H, part AA' syst. AA'BB', $J_{5,6}$=10.1 Hz, CH=CHCO), 6.21 (2H, part AA' syst. AA'BB', $J_{5,6}$=10.1 Hz, CH=CHCO), 6.09 (2H, part BB' syst. AA'BB', $J_{6,5}$=10.1 Hz, CH=CHCO), 6.08 (2H, part BB' syst. AA'BB', $J_{6,5}$=10.1 Hz, CH=CHCO), 3.76 (6H, s, $OCH_3$), 2.81 (2H, s, $CH_2$), 2.80 (2H, s, $CH_2$), 0.24 (9H, s, $Si(CH_3)_3$), 0.23 (9H, s, $Si(CH_3)_3$).

Example 12

Preparation of rac-4R,5S,6S)-1-benzyloxy-5,6-dimethylmethylendioxy-1-azaspiro[3.5]nona-8-ene-2,7-dione (13)

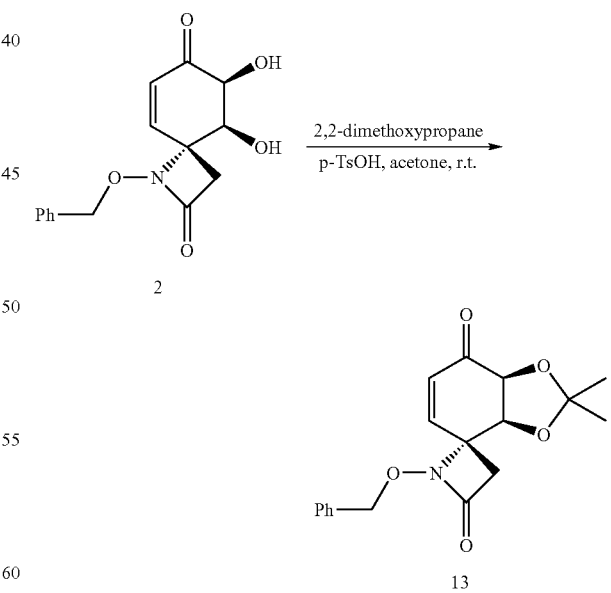

To a stirred solution of rac-(4R,5S,6S)-1-benzyloxy-5,6-dihydroxy-1-azaspiro[3.5]nona-8-ene-2,7-dione (2) (109 mg, 0.377 mmol) and 2,2-dimethoxypropane (0.24 ml, 1.885 mmol) in dry acetone (0.75 ml) was added at room temperature catalytic amount of p-TsOH (1% mmol). The resulting mixture was stirred at room temperature for 18 h, then quenched with saturated aqueous Na$_2$CO$_3$ solution (1 ml) and extracted with AcOEt (3×2 ml). The combined organic extracts were washed with brine (3 ml), dried over Na$_2$SO$_4$, filtered and concentrated under reduced pressure. The residue was purified by silica gel column chromatography (hexane-AcOEt, 5:2) to give rac-(4R,5S,6S)-1-benzyloxy-5,6-dimethylmethylendioxy-1-azaspiro[3.5]nona-8-ene-2,7-dione (13) as a solid (52 mg, 42%).

R$_f$=0.50 (TLC, hexane-AcOEt, 1:1); yield, 42%; solid; $^1$H-NMR (200 MHz, CDCl$_3$): δ 7.50-7.22 (5H, m, Ph), 6.28 (1H, part A syst. AB, J$_{9,8}$=9.9 Hz, H-9), 5.91 (1H, part B syst. AB, J$_{8,9}$=9.9 Hz, H-8), 4.95 (1H, part A syst. AB, J=11.4 Hz, OC$\underline{H}_2$Ph), 4.85 (1H, part B syst. AB, J=11.4 Hz, OC$\underline{H}_2$Ph), 4.27 (1H, part A syst. AB, J=5.1 Hz, H-5 or H-6), 4.11 (1H, part B syst. AB, J=5.1 Hz, H-6 or H-5), 6.37 (1H, part A syst. AB, J=15.0 Hz, CH$_2$), 2.79 (1H, part B syst. AB, J=15.0 Hz, CH$_2$), 1.34 (3H, s, CH$_3$), 1.27 (3H, s, CH$_3$).

The invention claimed is:

1. A compound of formula I

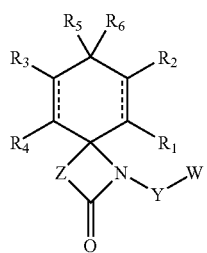

formula I wherein
- R$_1$, R$_2$ are each independently selected from H, OH or OPr; or R$_1$ and R$_2$ together are O—X$_1$—O;
- R$_3$, R$_4$ are each independently selected from H, OH or OPr; or R$_3$ and R$_4$ together are O—X$^2$—O;
- R$_5$ and R$_6$ together are =O or R$_5$ is selected from H, OH, OPr or R$_5$ and R$_3$ together are O—X$_3$—O or R$_5$ and R$_2$ together are O—X$_4$—O and R$_6$ is selected from hydrogen, cyano, substituted or unsubstituted alkyl, substituted or unsubstituted cycloalkyl, substituted or unsubstituted alkenyl, substituted or unsubstituted alkynyl, substituted or unsubstituted aryl, substituted or unsubstituted heterocyclyl, with the proviso that at least one of R$_1$, R$_2$, R$_3$, R$_4$ or R$_5$ is OH or OPr;
- Pr is an hydroxy protecting group which can be the same or different on each of R$_1$, R$_2$, R$_3$, R$_4$ or R$_5$;
- X$_1$X$_2$, X$_3$ and X$_4$ are each independently a divalent hydroxyl protecting group;
- the dotted line represents a single or double bond with the proviso that when both R$_1$ and R$_2$, or R$_3$ and R$_4$, are H then there is a double bond between the two C to which the H are linked;
- Z is —(CRaRb)$_n$— wherein n is 1, and Ra and Rb are each independently selected from hydrogen, substituted or unsubstituted alkyl, substituted or unsubstituted cycloalkyl, substituted or unsubstituted alkenyl, substituted or unsubstituted aryl, substituted or unsubstituted heterocyclyl, substituted or unsubstituted alkoxy, substituted or unsubstituted aryloxy, substituted or unsubstituted amino or halogen;
- Y is selected from —O—, —S—, or —C(O)—;
- W is a group selected from substituted or unsubstituted arylalkyl, substituted or unsubstituted heterocyclylalkyl, substituted or unsubstituted alkenyl;

or a salt thereof.

2. A compound according to claim 1 characterized in that Z is —(CHRa)$_n$—, Ra and n being as defined in claim 1.

3. A compound according to claim 1 characterized in that Z is —CH$_2$—.

4. A compound according to claim 1 characterized in that Y is —O—.

5. A compound as defined in claim 1 characterized in that W is —CRaRb-Q, wherein Ra and Rb are as previously defined and Q is substituted or unsubstituted aryl, substituted or unsubstituted heterocyclyl, substituted or unsubstituted alkenyl.

6. A compound as defined in claim 5 characterized in that Ra and Rb are H.

7. A compound as defined in claim 5 characterized in that Q is aryl.

8. A compound as defined in claim 1 characterized in that the hydroxyl protecting group Pr is independently selected from alkylsilyl, alkyl, allyl; alkoxymethyl, aryloxymethyl, acetyl, benzoyl, pivaloyl, methoxyacetyl, chloroacetyl, levulinyl, methoxycarbonyl, benzyloxycarbonyl, p-nitrobenzyloxycarbonyl, tert-butoxycarbonyl, 2,2,2-trichloroethoxycarbonyl, 2-(trimethylsilyl)ethoxycarbonyl and allyloxycarbonyl.

9. A compound according to claim 1 having formula II

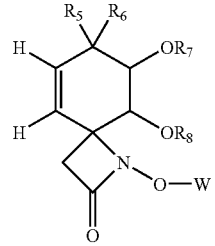

formula II wherein
- R$_7$ and R$_8$ are independently selected from H or Pr;
- W, R$_5$ and R$_6$ are as defined in claim 1.

10. A compound according to claim 1 having formula III

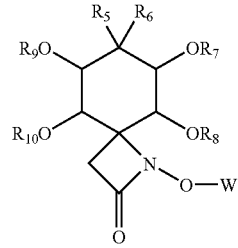

formula III wherein R$_7$, R$_8$, R$_9$ and R$_{10}$ are each independently selected from H or Pr;
- W and R$_5$, R$_6$ are as defined in claim 1.

11. A compound according to claim 9 wherein there are at least 2 different protecting groups Pr on R$_5$, R$_7$, R$_8$, R$_9$ and R$_{10}$.

12. A compound according to claim 1 which corresponds to any of the following formulae A to L:
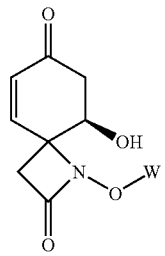
A
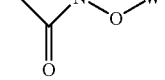
B
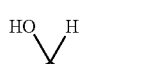
C
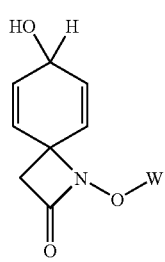
D
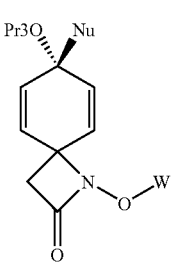
E
-continued
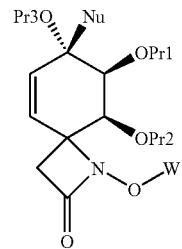
F
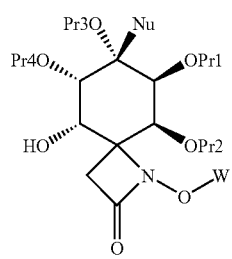
G
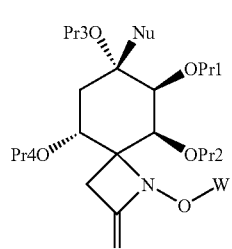
H
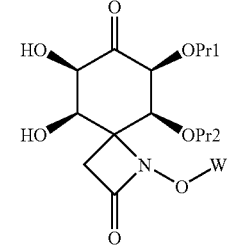
I
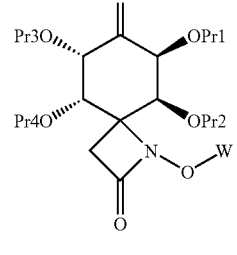
J
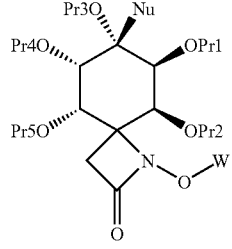
K -continued

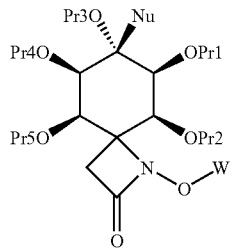

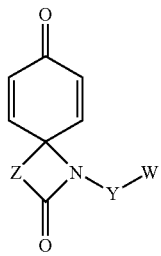

formula IV wherein W is as defined in claim 1; $Pr_1$ to $Pr_5$ are hydroxyl protecting groups which can be independently the same or different on each hydroxyl and can optionally protect at the same time two hydroxyl groups, and Nu is a group added by nucleophilic attack at the carbonyl group; their diastereoisomers, enantiomers and mixtures thereof.

13. A compound according to claim 12 wherein Nu is selected from the group consisting of hydride, CN, substituted or unsubstituted alkyl, substituted or unsubstituted cycloalkyl, substituted or unsubstituted alkenyl, substituted or unsubstituted alkynyl, substituted or unsubstituted aryl, and substituted or unsubstituted heterocyclyl.

14. A process for the preparation of a compound according to claim 1 comprising a first reaction selected from the group consisting of nucleophilic attack on the carbonyl group, and hydroxylation or dihydroxylation applied to a starting material of formula IV:

wherein Z, Y and W are as defined in claim 1;
  and optionally further comprising in any order one or more steps selected from the group consisting of:
  a) hydroxylation or dihydroxylation
  b) hydroxyl or carbonyl protection
  c) nucleophilic attack on the carbonyl group
  d) hydroxyl inversion.

15. A compound as defined in claim 7, wherein Q is phenyl.

16. A compound according to claim 1, wherein O—$X_1$—O, O—$X_2$—O, O—$X_3$—O and O—$X_4$—O are independently selected from the group consisting of isopropylidene acetal, cyclohexylidene acetal, cyclopentylidene acetal, arylmethylene acetals, methylene acetals, diphenylmethylene acetal, and 1,1,3,3-tetraisopropyl disiloxanylidene acetal.

* * * * *